Figure 1:
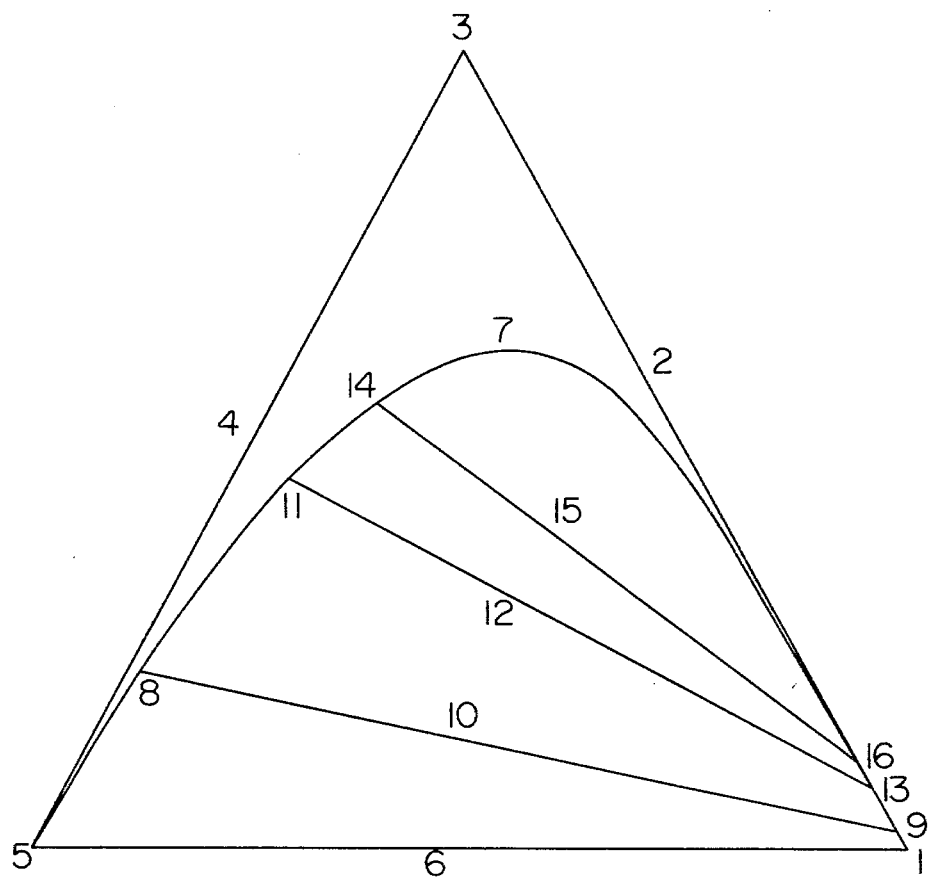

United States Patent [19]
Mori et al.

[11] 4,328,377
[45] May 4, 1982

[54] PROCESS FOR PRODUCING PHENOLIC COMPOUNDS

[75] Inventors: Akira Mori, Funabashi; Sekijiro Noda, Ichihara; Hiroshi Osuo, Ichihara; Akio Kanazawa, Ichihara; Tadahiko Nishimura, Iwakuni; Masatoshi Yamamoto; Yoshio Tomatsu, both of Ichihara, all of Japan

[73] Assignee: Mitsui Petrochemical Industries Ltd., Tokyo, Japan

[21] Appl. No.: 204,172

[22] Filed: Nov. 5, 1980

[30] Foreign Application Priority Data

Nov. 5, 1979 [JP] Japan .................................. 54-141993

[51] Int. Cl.³ .............................................. C07C 37/08
[52] U.S. Cl. .................................... 568/798; 568/768; 568/754
[58] Field of Search ...................... 568/798, 768, 754

[56] References Cited
U.S. PATENT DOCUMENTS 3,169,101  2/1965  Berthoux ............................ 568/754
4,251,325  2/1981  Marsh et al. ........................ 568/754

FOREIGN PATENT DOCUMENTS 50-1258   1/1975  Japan .
743004    1/1956  United Kingdom .
805048   11/1958  United Kingdom .
1394452   5/1975  United Kingdom ................. 568/754

Primary Examiner—Werren B. Lone
Attorney, Agent, or Firm—Sherman & Shalloway

[57] ABSTRACT

In a process for producing a phenolic compound which comprises treating an aralkyl hydroperoxide with a mineral acid to cleave it to phenolic compound and a ketone, neutralizing or removing the mineral acid, feeding the resulting acid cleavage mixture containing the salt to a distillation column, distilling it therein to separate it into an overhead fraction consisting mainly of the ketone and a bottom fraction consisting mainly of the phenolic compound, and recovering the phenolic compound from the bottom fraction; the improvement which comprises withdrawing a liquid layer from a site of feeding the acid cleavage mixture in the distillation column or from a site below it but above the bottom of the distillation column, subjecting the liquid layer to an oil-water separating means, recycling the separated oil layer to a site below said site of withdrawal, optionally feeding a hydrocarbon having a lower boiling point than the phenolic compound but a higher boiling point than the keton and/or water to the distillation column, and recovering the phenolic compound from the bottom fraction whose salt content has thus been reduced.

13 Claims, 2 Drawing Figures

PROCESS FOR PRODUCING PHENOLIC COMPOUNDS

This invention relates to an improved process for producing phenolic compounds, and particularly, to an industrially improved process for the production of phenolic compounds in pure form by the catalytic acid cleavage of aralkyl hydroperoxides such as cumene hydroperoxide.

Conventional industrial production of phenolic compounds comprises cleaving aralkyl hydroperoxides of the general formula

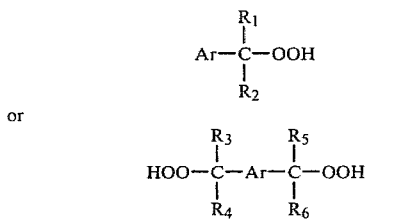

wherein Ar represents an aromatic ring, preferably a phenyl ring, and $R_1$, $R_2$, $R_3$, $R_4$, $R_5$, and $R_6$, independently from each other, represent a lower alkyl group, provided that the total number of carbon atoms of $R_1$ and $R_2$, or $R_3$ and $R_4$, or $R_5$ and $R_6$, respectively, does not exceed 4, with mineral acids, and recovering the desired phenolic compounds from the acid-cleavage reaction mixtures. For example, phenol is produced by contacting cumene hydroperoxide obtained by air oxidation of cumene with a mineral acid such as sulfuric acid, phosphoric acid or hydrochloric acid to cleave it, and subjecting the resulting acid cleavage mixture containing phenol and acetone as main products to a suitable separating means such as distillation to separate and recover phenol.

When the acid cleavage mixture is directly subjected to the separating step in an attempt to recover the desired phenolic compound, the presence of the mineral acid in the mixture will corrode the apparatuses used in the recovering step, such as a distillation column, and side-reactions may take place in the separating step such as distillation. It is the usual practice therefore to remove the mineral acid contained in the acid cleavage mixture before the separating step by neutralizing it with a strong alkali such as sodium hydroxide or sodium phenolate. Neutralization of the mineral acid poses a new problem. When sulfuric acid is used as the mineral acid and sodium hydroxide is used as the strong alkali, sodium sulfate forms as a result of neutralization. A salt of this kind cannot be sufficiently removed from the mixture by a simple means. When the mixture containing the remaining salt is fed to a distillation column, the salt often clogs a reboiler used for heating. Consequently, it is necessary to stop the operation of the distillation system incessantly so as to remove the clogging salt from the reboiler. Furthermore, because a large quantity of the salt is accumulated in a high-boiling tarry material left as a by-product after removing the phenol and ketone and low-boiling fractions from the cleavage mixture, the value of the tarry material as a fuel is reduced.

Various methods have therefore been proposed up to date in order to minimize the amount of the salt in the acid cleavage mixture which is to be fed to a step of recovering a phenolic compound. For example, British Patent Specification No. 743,004 discloses a method which comprises contacting the acid cleavage reaction product containing a mineral acid with an aqueous solution of a strong alkali such as sodium phenolate, subjecting the mixture to an oil-water separating means, and washing the resulting oil layer with water. Tracing of this method by the present inventors has shown that when the acid cleavage mixture containing a mineral acid is contacted with an aqueous solution of a strong alkali, emulsification occurs vigorously, and unless a large quantity of water is used in washing the oil layer, the salt cannot be sufficiently removed. When a large amount of water is used to remove the salt, however, large quantities of the desired phenolic compound and ketone move to the water layer, and therefore, as disclosed in the above-cited British Patent Specification, an additional device for recovering these substances from the water layer is required. If the oil layer is washed with a small quantity of water which does not require such a recovering device, the salt remains in an amount on the order of several hundred ppm or more in the oil layer and washing with water is not entirely effective.

British Patent Specification No. 805,048 proposes a method which comprises contacting the acid cleavage reaction mixture with an aqueous solution containing a salt in a high concentration and having a pH of not more than 7 to extract the mineral acid into the water layer, subjecting the oil layer after oil-water separation to a recovering step, and meanwhile, neutralizing the water layer having the mineral acid extracted thereinto with a strong alkali. Tracing of this method by the present inventors showed that in contrast to the method of British Pat. No. 743,004, emulsification does not occur, and the amounts of the phenolic compound and ketone which move to the water layer are small and the amount of water to be discharged out of the system can be small; but that in spite of these advantages, since the aqueous solution containing the same salt in a high concentration gets mixed in atomized form with the oil layer when the acid cleavage mixture is contacted with the aqueous solution containing the salt in a high concentration, the salt is present in the oil layer in an amount on the order of 100 ppm or more.

Accordingly, it is usual that even after performing the step of removing the mineral acid, the acid cleavage mixture to be fed to the step of recovering the desired phenolic compound still contains the mineral acid salt in an amount on the order of more than about 100 ppm. Moreover, the mineral acid salt is contained in such a manner that the water layer containing the salt is dispersed in atomized form. It is difficult therefore to separate and remove the salt substantially completely by a commercially feasible method.

Thus, the acid cleavage mixture containing a small amount of the mineral acid salt has to be fed to the step of recovering the phenolic compound, and the aforesaid inconvenience in the distillation column and other inconveniences still remain uneliminated.

It is an object of this invention to provide an improved process for producing phenolic compounds, which is free from the aforesaid defects.

According to this invention, there is provided, in a process for producing a phenolic compound which comprises treating an aralkyl hydroperoxide with a mineral acid to cleave it to a phenolic compound and a ketone, neutralizing or removing the mineral acid, feeding the resulting acid cleavage mixture containing the salt to a distillation column, distilling it therein to separate it into an overhead fraction consisting mainly of the ketone and a bottom fraction consisting mainly of the phenolic compound, and recovering the phenolic compound from the bottom fraction, the improvement which comprises withdrawing a liquid layer from a site of feeding the acid cleavage mixture in the distillation column or from a site below it but above the bottom of the distillation column, subjecting the liquid layer to an oilwater separating means, recycling the separated oil layer to a site below said site of withdrawal, optionally feeding a hydrocarbon having a lower boiling point than the phenolic compound but a higher boiling point than the ketone and/or water to the distillation column, and recovering the phenolic compound from the bottom fraction whose salt content has thus been reduced.

The process which comprises treating an aralkyl hydroperoxide with a mineral acid to cleave it, removing the mineral acid, distilling the acid cleavage reaction mixture to collect a ketone and components having a lower boiling point than the ketone from the top of the distillation column and separating a fraction containing the phenolic compound as a bottom fraction, and recovering the phenolic compound from the bottom fraction is disclosed in Japanese Patent Publication No. 1258/75 as an initial step forming part of a series of steps for producing phenol of higher purity from the acid cleavage product of cumene hydroperoxide. When in the production of industrially high purity phenol by the cumene method, a step of oxidizing cumene with molecular oxygen to produce cumene hydroperoxide, a step of catalytically cleaving cumene hydroperoxide with a mineral acid and a step of removing the mineral acid by neutralization are performed under proper conditions, and the resulting acid cleavage product free from the mineral acid is distilled by the known method described in the abovecited Japanese Patent Publication No. 1258/75, the bottom fraction is an emulsion in view of its composition, and its separation into a water layer and an oil layer is extremely difficult. Consequently, the salt is difficult to remove, and even when the subsequent step of recovering phenol of high purity which is disclosed in the above-cited Japanese Patent Publication is used, the aforesaid inconvenience is caused. This inconvenience can be completely eliminated, however, by using the aforesaid improved process of this invention instead of the initial distillation step disclosed in the abovecited Japanese Patent Publication. The specific case disclosed in the above Japanese Patent Publication is not the only case in which the process of this invention is effective. According to the process of this invention, even when the acid cleavage product of an aralkyl hydroperoxide from which the mineral acid has been removed contains the salt in an amount of as large as more than 100 ppm, the salt content of the bottom fraction consisting mainly of a phenolic compound in the initial distillation step of removing the ketone for recovery of the phenolic compound from the acid cleavage mixture can be drastically decreased. Accordingly, whatever method is used in the subsequent step of recovering the phenolic compound, the inconveniences of the prior art, such as the clogging of the reboiler used in the distillation column, and the problem of the salt content in by-product tarry materials occurring in the step of producing hydroperoxide and in the step of acid cleaving hydroperoxide, can all be eliminated.

Figure 2:
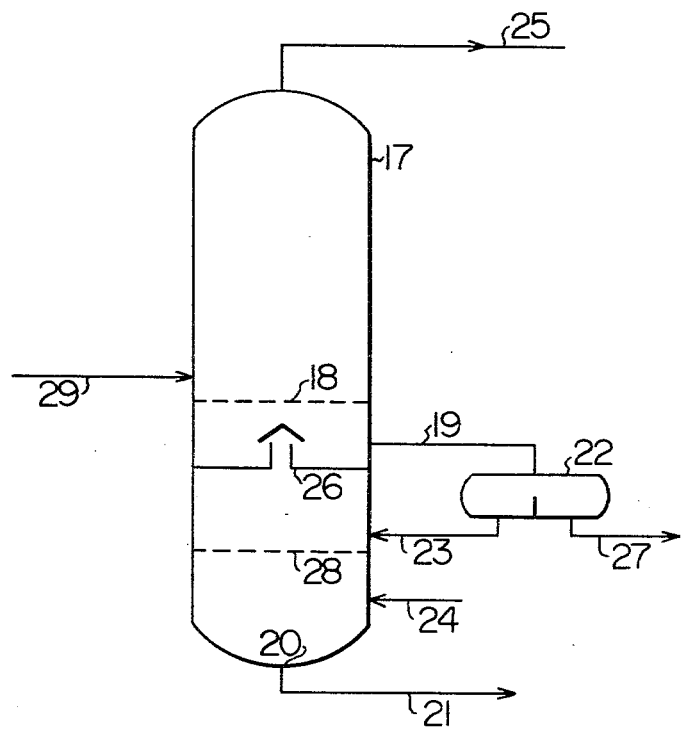

The process of this invention is described below in greater detail with the aid of the accompanying drawings in which:

FIG. 1 is a triangular coordinate showing the mutual solubilities of three components, phenol, water and hydrocarbon; and FIG. 2 is a schematic side elevation view of a distillation apparatus which can be used to perform the process of this invention.

In the first step of the process of this invention, an aralkyl hydroperoxide is treated with a mineral acid to cleave it to a phenolic compound and a ketone.

The aralkyl hydroperoxide used in the process of this invention includes compounds of formulae (I) and (II) given hereinabove (in these formulae, the lower alkyl group for $R_1$ through $R_6$ is a linear or branched alkyl group containing up to 3, preferably up to 2, carbon atoms). Specific examples of the aralkyl hydroperoxide are cumene hydroperoxide, p-cymene hydroperoxide, m-cymene hydroperoxide, sec-butylbenzene hydroperoxide, p-ethylisopropylbenzene hydroperoxide, isopropylnaphthalene hydroperoxide, m-diisopropylbenzene dihydroperoxide and p-dihydroperoxide. Cumene hydroperoxide, p-cymene hydroperoxide and m-cymene hydroperoxide are preferred. Cumene hydroperoxide is most preferred.

The mineral acid as a catalyst for cleaving the hydroperoxide into a phenolic compound and a ketone preferably includes sulfuric acid, hydrochloric acid, phosphoric acid and mixtures of these. Sulfuric acid is especially preferred.

The phenolic compound, the desired product of the process of this invention is expressed by the formula Ar-OH or HO-Ar-OH corresponding to formula (I) or (II).

Specific examples are phenol, p-cresol, m-cresol, ethylphenol, naphthol, hydroquinone and resorcinol. Phenol, p-cresol and m-cresol are preferred, and phenol is most preferred.

The ketone, another acid cleavage product, is expressed by the formula

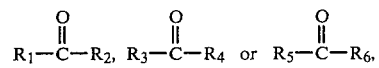

and specifically includes acetone and methyl ethyl ketone. When the ketone is acetone, the process of this invention proceeds most conveniently.

Any known method can be employed to cleave the hydroperoxide with a mineral acid. Industrially, the cleavage reaction is usually performed in the presence of a hydrocarbon solvent. An aromatic hydrocarbon is preferred as the hydrocarbon solvent, and specific examples include benzene, toluene, xylene, cumene, cymene, ethylbenzene, diisopropylbenzene, butylbenzene, alpha-methylstyrene and isopropenyltoluene. The temperature of the acid cleavage is not particularly restricted. Advantageously, it is generally about 50° C. to about 100° C., preferably about 70° C. to about 90° C.

The amount of the mineral acid used in the catalytic acid cleavage is neither critical, and can be varied widely according to the type of the hydroperoxide and/or the mineral acid. Generally, the amount of the mineral acid is 0.05 to 2 parts by weight, preferably 0.1 to 1 part by weight, per 100 parts by weight of the hydroperoxide to be cleaved.

The mineral acid contained in the reaction mixture obtained by the acid cleavage of the hydroperoxide is then neutralized or removed. The acid cleavage mixture so treated is then subjected to a step of recovering the phenolic compound as will be described hereinbelow.

The neutralization of the acid cleavage mixture of the hydroperoxide or the removal of the mineral acid from it can be performed by any desired known method. It has been found that in the process of this invention, a salt formed as a result of the neutralization of the acid cleavage needs not always to be separated and removed from the acid cleavage mixture. Desirably, at least a part of the salt should be removed. For example, the neutralization of the acid cleavage mixture is carried out by a method which comprises contacting the acid cleavage mixture with an aqueous solution of a strong alkali such as sodium hydroxide or sodium phenolate and then optionally removing the water layer by an oil-water separation procedure; a method which comprises contacting the acid cleavage mixture containing a mineral acid with an aqueous solution of a strong alkali such as sodium hydroxide, subjecting it to an oil-water separation procedure, and washing the oil layer with water; a method which comprises directly adding an alkaline substance to the acid cleavage mixture; or a method which comprises filtering the as-neutralized mixture to remove the salt precipitated in solid form.

On the other hand, the mineral acid may be removed by an extractive separating method, such as the method disclosed in British Patent Specification No. 805,048 which comprises contacting the acid cleavage mixture with an aqueous solution containing a salt in a high concentration and having a pH of not more than 7 to extract and remove the mineral acid from the mixture. It has been ascertained by the experiments of the present inventors that in this extracting method, the pH of the aqueous solution to be contacted with the acid cleavage mixture needs not always to be not more than 7, and an aqueous solution containing a salt and having a pH in the range of 7 to 11, such as an aqueous solution containing 2 to 25% by weight of sodium sulfate and having a pH of 7 to 11, can also be used.

The minimum degree of neutralization of the acid cleavage mixture or removal of the mineral acid from the mixture is such that the cleavage mixture after neutralization or removal of the acid does not substantially corrode apparatuses used in the subsequent steps. Specifically, it is such that when the acid cleavage mixture after neutralization or removal of the mineral acid is contacted vigorously with an equal volume of water, the pH of the resulting aqueous layer is higher than 5.

The composition of the acid cleavage mixture resulting after the neutralization or removal of the mineral acid varies depending upon the type of the starting hydroperoxide, the type of the mineral acid, the degree of acid cleavage, the method of neutralization or removal of the mineral acid, etc., and cannot be definitely determined. A typical example of the composition is as follows:

Ketones: 15 to 60% by weight
Phenolic compond: 20 to 60% by weight
Hydrocarbons (derived mainly from the solvent used in the acid cleavage reaction): 5 to 60% by weight
Water: 5 to 20% by weight
Salts: about 50 ppm to several thousand ppm The acid cleavage mixture after the neutralization or removal of the mineral acid is then subjected to a step of recovering the resulting phenolic compound. In the process of this invention, the acid cleavage mixture is first distilled in a distillation column. The distilling operation is most important in the process of this invention.

In the distillation column, a relatively low-boiling fraction consisting mainly of a ketone is distilled off from the acid cleavage mixture through the top of the column, and on the other hand, a relatively high-boiling fraction consisting mainly of the phenolic compound is withdrawn as a bottom fraction.

The main purpose of the distillation operation is to remove the ketone from the acid cleavage mixture containing the salt and simultaneously to obtain a bottom fraction having a low salt content and consisting mainly of the phenolic compound.

The distillation can generally be performed by using a multi-tray distillation column or a packed column, but the use of the multi-tray distillation column is preferred.

The following embodiment involves the use of the multi-tray distillation column, but the packed column may be used equally. It should be understood in this regard that trays in a multi-tray distillation column denote positions corresponding to these trays when another type of distillation column is referred to.

The above distillation operation can be performed by using a multi-tray distillation column having at least 20, preferably at least 30, trays. The distillation pressure is not critical, and is usually about 250 mmHg (absolute) to about 2 kg/cm$^2$.G, preferably about 300 mmHg (absolute) to atmospheric pressure.

The acid cleavage mixture may be fed to any desired site of the multi-layer distillation column. Generally, it is desirable to feed the acid cleavage mixture to a tray located at a height about ⅓ to about 170 of the entire height of the column from its bottom.

The process of this invention is characterized by the fact that the liquid layer is withdrawn from a tray of the multi-tray distillation column to which the acid cleavage mixture is fed or from a tray below it but above the bottom of the distillation column, and subjected to an oil-water separating means, and the oil layer separated is recycled to a tray located at a lower position than the tray from which the liquid layer has been withdrawn.

The purpose of withdrawing the liquid layer, subjecting it to an oil-water separating means and recycling the separated liquid layer to the distillation column is to remove out of the system the aqueous layer in which the salt is dissolved by the oil-water separation and thereby to obtain a bottom fraction having a low salt content.

The "aqueous layer", as used herein, denotes a layer having a relatively high water content, and the "oil layer" denotes the other layer having a relatively low water content.

In the industrial practice of the process of this invention, it is important that the liquid layer withdrawn as above can be very easily separated into an oil layer and an aqueous layer. For this purpose, it is important that the liquid layer to be withdrawn should form a heterogeneous system composed of an oil layer consisting mainly of the phenolic compound and hydrocarbons and an aqueous layer consisting mainly of water. It is very desirable that when the withdrawn liquid layer is allowed to stand, it is clearly separated into an upper layer composed of the oil layer and a lower layer composed of the aqueous layer within a relatively short period of time. In order that such layer separation takes place easily within a short period of time, the difference in specific gravity between the oil layer and the aqueous layer should be at least 0.03, preferably at least 0.04.

Accordingly, when the tray from which the liquid layer is withdrawn in accordance with the process of this invention is preferably that tray which is below the tray to which the acid cleavage mixture is fed, and in which the liquid layer forms a heterogenous system composed of an oil layer and an aqueous layer and the difference in specific gravity between the oil layer and the aqueous layer is at least 0.03, preferably at least 0.04.

On the other hand, the hydrocarbon content of the liquid layer in the withdrawing tray is desirably as high as possible, and it is most suitable to withdraw the liquid layer from an intermediate tray in which the hydrocarbon content of the liquid layer is maximum. This is not absolutely necessary, and it is possible to withdraw the liquid layer from an intermediate tray in which the hydrocarbon content of the oil layer is generally at least 35% by weight, preferably at least 40% by weight.

Depending upon the composition of the acid cleavage mixture to be fed to the multi-layer multi-tray distillation column in accordance with this invention, the liquid layer in an intermediate tray may not form a heterogeneous system, or may form a heterogenous system in which the difference in specific gravity between the oil layer and the aqueous layer is not within the above-specified range or the hydrocarbon content of the liquid layer is not within the above-specified range. This situation arises, for example, when the acid cleavage mixture after the neutralization or removal of the mineral acid contains only a small amount of water, or has a low hydrocarbon content. In such a situation, a hydrocarbon having a lower boiling point than the phenolic compound present in the acid cleavage mixture and a higher boiling point than the ketone therein, and/or water is fed into the distillation column. There is no strict limitation on the site of feeding the additional compound. When water is to be fed, it is generally recommended that it should be fed to a tray located at a lower site than the withdrawing tray for the liquid layer, or it may be fed to the bottom of the distillation column. When a hydrocarbon is to be fed, the site of its feeding is not restricted. Preferably, it is fed into the tray to which the cleavage mixture has been fed, or to a lower tray. Alternatively, it may be added in advance to the acid cleavage mixture.

The hydrocarbon that can be fed has a higher boiling point than the ketone contained in the acid cleavage mixture and a lower boiling point than the phenolic compound contained on it. Specific examples of the hydrocarbon are linear or branched higher (preferably $C_6$ to $C_{10}$) alkanes such as hexane, heptane, octane, nonane, decane and isooctane, $C_6$-$C_{10}$ cycloalkanes such as cyclohexane, cycloheptane, cyclooctane, cyclononane and cyclodecane, and $C_6$-$C_{12}$ aromatic hydrocarbons such as benzene, toluene, xylene, ethylbenzene, cumene, cymene, alpha-methylstyrene, styrene, isopropenyltoluene, m-diisopropylbenzene, and p-diisopropylbenzene. These hydrocarbons may be used singly or in combination with each other. Of these, the aromatic hydrocarbons are preferred. For commercial application, the same aromatic hydrocarbon as used in the step of cleaving the hydroperoxide as a solvent is preferably used.

The hydrocarbon and/or water can be fed in the form of a liquid or a vapor. The amount of the hydrocarbon and/or water depends upon the composition of the acid cleavage mixture left after the neutralization or removal of the mineral acid such a compound is fed in such an amount that a liquid layer in a specified heterogeneous system mentioned hereinabove is present in an intermediate tray between the bottom of the distillation column and the tray to which the acid cleavage mixture has been supplied. It is very easy to those skilled in the art to determine the amount of such a compound in this way.

The amount of the liquid layer to be withdrawn is not critical, and can be varied widely according to the composition of the acid cleavage mixture to be fed into the distillation column, the distillation conditions, etc. Generally, all of the liquid layer in a given tray can be withdrawn.

The liquid layer withdrawn from the intermediate tray is separated into an oil layer and an aqueous layer by a known oil-water separating method such as a stationary separating method or a centrifugal separating method. Usually, all the oil layer separated is recycled to a tray located below the tray from which the liquid layer has been withdrawn. Preferably, it is recycled to a tray immediately before the withdrawing tray. The approximate composition of the oil layer to be recycled varies considerably depending upon the acid cleavage mixture fed to the distillation column, the site of withdrawal, etc.

In the meantime, the aqueous layer separated contains a large amount of the salt dissolved, and is to be removed out of the system. Since it also contains a small amount of the phenolic compound, it may optionally be supplied to a separate step of recovering the phenolic compound.

The aforesaid withdrawal of the liquid layer from the intermediate tray of the distillation column is described in more detail below.

A relatively high boiling fraction resulting from substantial removal of the ketone from the acid cleavage mixture left after neutralization or removal of the mineral acid is a mixture of the phenol compound, water, the aromatic hydrocarbon used as a solvent in the acid cleavage step, by-product aromatic hydrocarbons, small amounts of ketones, and other various by-products and the hydrocarbon and/or water optionally supplied to the distillation column. That the concentrations of water and hydrocarbons having a lower boiling point than the phenolic compound can be made higher in a certain position in an intermediate tray than at the bottom of the distillation column and the concentration of the phenolic compound can be made lower in an intermediate tray than at the bottom of the distillation column will be quite easily understandable to those skilled in the art in view of the essence of the process of this invention which involves distilling off low-boiling ketones from the top of the column and the phenolic compound from the bottom of the column. The liquid layer at a certain site in an intermediate tray in which the concentrations of the hydrocarbons and water are high and the concentration of the phenolic compound is low shows a strong tendency toward becoming a heterogeneous system composed of an oil layer and an aqueous layer. Since in the oil layer, the concentration of the hydrocarbons having a low specific gravity is high and the concentration of the phenol having a higher specific gravity is low, the specific gravity of the oil layer as a whole is low. On the other hand, the aqueous layer has a slightly lower content of the phenol, but its specific gravity is close to that of water. Accordingly, at an intermediate tray, the difference in specific gravity between the oil layer and the aqueous layer is generally larger than at the bottom of the distillation column. Since the concentration of the hydrocarbon can be changed as desired by externally feeding it, the specific gravity of the oil layer can be made close to the specific gravity (about 0.79 to about 0.82 at 100° C.) of the hydrocarbon. As the proportion of the hydrocarbon in the liquid layer becomes larger, the specific gravity of the aqueous layer approaches the specific gravity (about 0.96 at 100° C.) of water. The presence of the aqueous layer can be ensured by supplying water to the distillation column as required. Accordingly, in the present invention, even when the difference in specific gravity between the oil layer and the aqueous layer in the bottom fraction is less than 0.03, it is possible to provide a liquid layer having a specific gravity difference of less than 0.03 surely in an intermediate tray.

For an understanding of this fact, reference is made to FIG. 1. In FIG. 1, apexes 3, 5 and 1 respectively represent phenol, a hydrocarbon typified by a mixture of cumene and alpha-methylstyrene, and water. Curve 7 is a solubility curve at about 100° C. Lines 10, 12 and 15 represent tie lines. A liquid layer having the composition represented by each tie line separates into an oil layer and a water layer at two intersecting points of each tie line with the solubility curve 7. In other words, the liquid layer separates into an oil layer having the composition at point 8, 11 or 14 and an aqueous layer having the composition at point 9, 13, or 16. The specific gravity ($d_1$) of the oil layer and the specific gravity ($d_2$) of the aqueous layer are as follows:

| Oil layer | 8 | 11 | 14 |
|---|---|---|---|
| Hydrocarbon (%) | 77 | 48 | 33 |
| $d_1$ | 0.846 | 0.907 | 0.938 |
| Aqueous layer | 9 | 13 | 16 |
| $d_2$ | 0.960 | 0.963 | 0.964 |
| Δd | 0.114 | 0.056 | 0.026 |

It is clear therefore that the difference in specific gravity increases with an increase in the hydrocarbon content.

It is possible to experimentally determine an area which forms an aqueous layer and an oil layer having a difference in specific gravity of at least 0.03 by utilizing the triangular coordinate and thus obtain parameters for setting the distillation operation. Thus, the position of withdrawing the liquid layer, the supply of water or hydrocarbon, and other distilling operations can be easily prescribed.

The process of this invention can be advantageously applied even when the bottom fraction resulting from removal of ketones and components having lower boiling points than the ketones from the acid cleavage mixture containing a salt left after neutralization or removal of the mineral acid forms an oil layer and an aqueous layer, and the difference in specific gravity between these layers is at least 0.03. According to the process of this invention, the salt can be removed with better efficiency by subjecting a liquid layer at an intermediate tray having such a composition that permits easy separation into an oil layer and an aqueous layer to an oil-water separating procedure. However, the process of this invention is most preferably applied when the bottom fraction does not form an oil layer and an aqueous layer, or forms an oil layer and an aqueous layer having a difference in specific gravity of less than 0.03. Thus, a fraction containing phenolic compounds and having a low salt content is withdrawn from the bottom of the column, and is supplied to the subsequent purifying step. The purifying step can be performed by a known method, for example, the methods described in Japanese Patent Publications Nos. 5979/59 and 5713/61.

One example of a distillation apparatus for distilling the acid catalytic acid cleavage mixture of the aralkyl hydroperoxide after neutralization or removal of the mineral acid is shown in FIG. 2. In FIG. 2, the reference numeral 17 represents a multi-tray distillation column, and a material feed tray 18 of the distillation column 17 or a certain intermediate tray 26 located below the tray 18 but above the bottom 20 of the distillation column is connected to an oil-water separator 22 through a line 19. The liquid layer in the intermediate tray 26 is withdrawn and supplied to the oil-water separator 22. In the meantime, an oil layer outlet of the oil-water separator 22 is connected to a tray 28 located below the intermediate tray 26 by a line 23. The oil layer separated is recycled to the distillation column. If required, a water supply pipe may be provided in the tray 28 located below the intermediate tray 26 so that water including steam may be supplied to the distillation column as required.

The distillation method in accordance with this invention in such a distilling apparatus is especially effective for removing the salt efficiently from the acid cleavage mixture having a specified composition. It is also effective for removing low-boiling fractions, high-boiling fractions and salts simultaneously from a liquid mixture containing water, components having a lower boiling point than water, components having a higher boiling point than the water and water-soluble salts. It is especially effective when the liquid mixture is a homogeneous system or an emulsion, and even after distilling off components having a lower boiling point than water from the top of the distillation column, the bottom fraction is still a homogeneous system or an emulsion. In the distillation apparatus shown in FIG. 2, the distillation operation is of course carried out such that a liquid layer which can be easily separated into an oil layer and an aqueous layer forms in the tray 18 or between the tray 18 and the bottom 20 of the column.

The distillation column 17 is an ordinary multi-tray distillation column, and the oil-water separator 22 is an ordinary oil-water separator. A socalled chimney tray or a tray of a like structure is used as the intermediate tray 26.

The process of the present invention described hereinabove provides the following technical advantages.

The process of this invention makes it possible to remove the salt efficiently from the acid cleavage mixture left after the neutralization or removal of the mineral acid. As a result, the fouling phenomenon of a heat exchanger such as a reboiler used in the step of purifying the phenolic compound is substantially avoided. While in the prior art the operation of the distillation column must be stopped in about one month to clean it, this is not necessary in accordance with this invention for at least half a year. At the same time, the salt content of the by-product high boiling compounds may sometimes be reduced by more than about 90%, and these by-products can be effectively used as an ordinary fuel.

The process of this invention is more specifically described below with reference to FIG. 2.

Cumene hydroperoxide was cleaved with sulfuric acid by a customary method. The acid cleavage product was treated with sodium hydroxide to neutralize sulfuric acid and remove it.

The resulting acid cleavage mixture had the following approximate composition.

| | |
|---|---|
| Phenol | 38.2% by weight |
| Acetone | 28.2% by weight |
| Cumene | 9.1% by weight |
| alpha-Methylstyrene | 4.1% by weight |
| Acetophenone | 1.0% by weight |
| Hydrocarbons of unknown structures | 10.0% by weight |
| Water | 9.4% by weight |
| Salt (calculated as sodium sulfate) | 117 ppm |

The acid cleavage mixture was fed at a flow rate of 100 parts per hour to the 25th tray of a multi-tray distillation column having about 50 trays through a line 29, and distilled under atmospheric pressure while maintaining the column top temperature at 56° C. and the column bottom temperature at 117° C. An acetone fraction was withdrawn at a rate of 27.7 parts by weight per hour from the top of the column through a line 25. The liquid layer on a chimney tray 26 located on the third tray from the bottom was withdrawn at a flow rate of 127.6 parts by weight per hour through a line 19 and fed to a decanter-type oil-water separator 22 where it was separated into an oil layer and an aqueous layer. The aqueous layer containing 332 ppm of the salt calculated as sodium sulfate was discharged at a rate of 32.6 parts by weight per hour through a line 27. At this time, the difference in specific gravity between the oil layer and the aqueous layer was 0.06, and the composition of the entire liquid layer withdrawn, and the composition of the oil layer was as follows:

| | Entire liquid layer (% by weight) | Oil layer (% by weight) |
|---|---|---|
| Phenol | 31.3 | 39.8 |
| Acetone | 4.2 | 5.7 |
| Cumene (a) | 17.9 | 24.2 |
| alpha-Methylstyrene (b) | 5.6 | 7.5 |
| Water | 29.8 | 7.7 |
| Other hydrocarbons (c) | 10.4 | 14.1 |
| Total hydrocarbons (a) + (b) + (c) | 33.9 | 45.8 |

The oil layer separated was recycled to the first tray 28 from the bottom of the column at a rate of 95 parts by weight per hour through a line 23. From a line 24, steam at 105° C. was fed to a site near the bottom of the column at a rate of 28.7 parts per hour. The steam used in heating the aqueous layer which was separated by the above oil-water separating procedure and recovered was used as this steam. A high boiling fraction having the following composition was withdrawn from the bottom 20 of the column through a line 21.

| | | |
|---|---|---|
| Phenol | 58.8% | by weight |
| Acetone | 1.9 | by weight |
| Cumene | 14.1 | by weight |
| alpha-Methylstyrene | 6.2 | by weight |
| Acetophenone | 1.6 | by weight |
| Hydrocarbons of unknown structures | 13.2 | by weight |
| Water | 4.2 | by weight |
| Salt (calculated as sodium sulfate) | 10 ppm | |

The content of the salt was determined by measuring the content of sodium and calculating it as sodium sulfate.

Clogging owing to fouling of the reboiler used in the step of distilling off compounds having a lower boiling point than phenol from the high-boiling fraction and the subsequent distilling step of removing compounds having a higher boiling point than phenol was not noted even after the operation was performed continuously for more than 6 months. The by-product high-boiling compounds obtained by the latter-mentioned distilling step had a salt content of as low as about 200 ppm, and can be fully used as a fuel for boilers.

For comparison, the same acid cleavage mixture as above was fed into the same distillation column as above except that it did not have the line 19, the oil-water separator 22, the line 23 and the line 24, and the acetone component was distilled off from the line 35. The salt content of the bottom fraction was about 150 ppm calculated as sodium sulfate. Moreover, the bottom fraction was vigorously emulsified, and could not be separated into an oil layer and an aqueous layer. After allowing it to stand for a long period of time, the specific gravities of the oil and aqueous layers were measured. The difference in specific gravity between them was 0.02.

What we claim is:

1. In a process for producing a phenolic compound which comprises treating an aralkyl hydroperoxide of the formula:

or

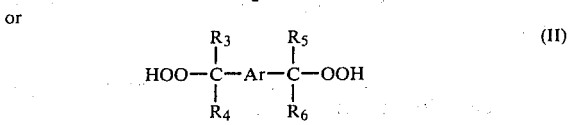

wherein Ar represents a phenyl ring and $R_1$, $R_2$, $R_3$, $R_4$, $R_5$ and $R_6$, independently of each other represent a lower alkyl group, provided that the total carbon atoms in $R_1$–$R_6$ does not exceed 4; with a mineral acid to cleave it to a phenolic compound of the formula:

wherein Ar is as defined above; and a ketone, neutralizing or removing the mineral acid, feeding the resulting acid cleavage mixture containing the salt to a distillation column, distilling it therein to separate it into an overhead fraction consisting mainly of the ketone and a bottom fraction consisting mainly of the phenolic compound, and recovering the phenolic compound from the bottom fraction; the improvement which comprises withdrawing a liquid layer from a site of feeding the acid cleavage mixture in the distillation column or from a site below it but above the bottom of the distillation column, subjecting the liquid layer to an oil-water separating means, recycling the separated oil layer to a site below said site of withdrawal, and recovering the phenolic compound from the bottom fraction whose salt content has thus been reduced.

2. The process of claim 1 wherein the liquid layer is a heterogeneous system composed of the oil layer and the water layer and the difference in specific gravity between the oil layer and the aqueous layer is at least 0.03.

3. The process of claim 1 wherein the oil layer contains at least 35% by weight of hydrocarbons.

4. The process of claim 1 wherein the liquid layer is withdrawn from a site below the site of feeding the acid cleavage mixture but above the bottom of the distillation column.

5. The process of claim 1 wherein the distillation column is a multi-tray distillation column.

6. The process of claim 5 wherein the multi-tray distillation column has at least 20 trays.

7. The process of claim 5 wherein the acid cleavage mixture is fed to a tray located at a height corresponding to about $\frac{1}{3}$ to about $\frac{2}{3}$ of the entire height of the distillation column.

8. The process of claim 1 wherein the aralkyl hydroperoxide is cumene hydroperoxide, p-cymene hydroperoxide or m-cymene hydroperoxide.

9. The process of claim 1 wherein the mineral acid is sulfuric acid.

10. The process of claim 1 wherein the bottom fraction is subjected to a purifying step for recovery of the phenolic compound.

11. The process of claim 1 wherein said improvement further comprises feeding a hydrocarbon having a lower boiling point than the phenolic compound but a higher boiling point than the ketone, water or a mixture thereof to the distillation column.

12. The process of claim 1 wherein the aralkyl hydroperoxide is a compound of Formula (I) and the phenolic compound is said compound of Formula Ar—OH.

13. The process of claim 2 wherein the difference in specific gravity between the oil layer and the aqueous layer is at least 0.04.

* * * * *